(12) United States Patent
Jalali et al.

(10) Patent No.: US 7,821,633 B2
(45) Date of Patent: Oct. 26, 2010

(54) APPARATUS AND METHOD FOR RAMAN SPECTROSCOPY AND MICROSCOPY WITH TIME DOMAIN SPECTRAL ANALYSIS

(75) Inventors: Bahram Jalali, Los Angeles, CA (US); Daniel Solli, Oakland, CA (US); Jason Chou, Walnut Creek, CA (US)

(73) Assignee: The Regents of the University of California, Oakland, CA (US)

( * ) Notice: Subject to any disclaimer, the term of this patent is extended or adjusted under 35 U.S.C. 154(b) by 28 days.

(21) Appl. No.: 12/210,656

(22) Filed: Sep. 15, 2008

(65) Prior Publication Data
US 2009/0073432 A1 Mar. 19, 2009

Related U.S. Application Data

(63) Continuation of application No. PCT/US2007/065393, filed on Mar. 28, 2007.

(60) Provisional application No. 60/787,129, filed on Mar. 28, 2006.

(51) Int. Cl.
G01J 3/44 (2006.01)
(52) U.S. Cl. ...................... 356/301; 356/73.1
(58) Field of Classification Search ............... 356/301, 356/73.1; 250/227.18
See application file for complete search history.

(56) References Cited

U.S. PATENT DOCUMENTS

| 5,243,983 | A | 9/1993 | Tarr et al. |
|---|---|---|---|
| 5,450,125 | A | 9/1995 | Ulich et al. |
| 6,151,522 | A * | 11/2000 | Alfano et al. ............... 600/473 |
| 6,174,677 | B1 | 1/2001 | Vo Dinh |
| 6,363,187 | B1 | 3/2002 | Fells et al. |
| 6,643,012 | B2 | 11/2003 | Shen et al. |
| 7,106,436 | B1 * | 9/2006 | Gord et al. .................. 356/301 |
| 7,352,469 | B2 * | 4/2008 | McGrew ..................... 356/451 |
| 2005/0012987 | A1 | 1/2005 | Okuno |
| 2005/0168735 | A1 | 8/2005 | Boppart et al. |
| 2008/0170218 | A1 * | 7/2008 | Dantus et al. ................. 356/39 |

FOREIGN PATENT DOCUMENTS

| WO | 2004073501 A2 | 9/2004 |
|---|---|---|
| WO | 2005008212 A2 | 1/2005 |

* cited by examiner

*Primary Examiner*—L. G Lauchman
(74) *Attorney, Agent, or Firm*—John P. O'Banion

(57) ABSTRACT

An apparatus and method for measuring Raman-type spectra using optical dispersion to convert an optical spectrum into a waveform which can be detected directly in the time domain without the use of a conventional spectrometer. In the example of stimulated Raman spectroscopy, the apparatus and method exposes a sample to a chirped, pulsed probe beam and a Raman pump beam and the resulting Raman spectra is detected by an optical detector in the time domain, and analyzed. Alternatively, the Raman spectra from the probe and pump beams is chirped with a dispersive element prior to detection and analysis. Each probe pulse provides a snapshot of the Raman spectrum that is sampled in time so that neither repetitive waveforms nor static samples are required. Therefore, high speed acquisitions and high throughput assays can be conducted. To facilitate detection, these spectral signals can also be amplified using distributed Raman amplification directly in the dispersive element.

54 Claims, 9 Drawing Sheets

APPARATUS AND METHOD FOR RAMAN SPECTROSCOPY AND MICROSCOPY WITH TIME DOMAIN SPECTRAL ANALYSIS

CROSS-REFERENCE TO RELATED APPLICATIONS

This application claims priority from, and is a 35 U.S.C. §111 (a) continuation of, co-pending PCT international application serial number PCT/US2007/065393, filed on Mar. 28, 2007, incorporated herein by reference in its entirety, which claims priority from U.S. provisional application Ser. No. 60/787,129 filed on Mar. 28, 2006, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention pertains generally to vibrational spectroscopy, and more particularly to an apparatus and method for Raman spectroscopy including sample exposure to a chirped, pulsed probe beam and a Raman pump beam wherein temporal dispersion is employed to transform the Raman-scattered light into a time-domain waveform which is electronically detected and preferably converted to digital signals.

2. Description of Related Art

Raman spectroscopy is widely used to study and identify a variety of biological, mineral, and chemical species. It is a powerful tool because it can uniquely identify molecules in complex mixtures and chemical environments, allowing for molecular fingerprinting and determination of relative concentration. Raman spectroscopy is a type of vibrational spectroscopy that observes radiation called the Raman spectrum scattered from an applied beam of light called the pump.

It has been observed that when a light beam is directed on a sample, photons are either absorbed by the sample material or scattered. Most of the photons are elastically scattered and have the same energy, frequency, and wavelength as the incident photons. This process is known as Rayleigh scattering. However, a small fraction of the incident radiation is inelastically scattered from optical phonons and shifted to different wavelengths and frequencies. This process is called Raman Scattering. The majority of Raman scattered photons shift to wavelengths, called the Stokes wavelengths, which are longer than the incident wavelength. A minority of Raman scattered photons shift to wavelengths, called the anti-Stokes wavelengths, which are shorter than the incident wavelength. Stokes scattering is more intense than anti-Stokes scattering because the Boltzmann occupation factor of vibrational energy levels above the ground state is small.

The Raman effect occurs when an incident photon interacts with the electric dipole of a molecule resulting in an energy transition from the molecular vibrations. With Stokes scattering, a vibrational transition is induced when a photon strikes the molecule and is re-emitted at a longer wavelength because some of the original energy of the photon has been transferred to the molecule. In the case of anti-Stokes scattering, the photon takes up part of the vibrational energy of a molecule, which is already in a higher vibrational state, and is emitted at a shorter wavelength. Therefore, Raman scattering arises from changes in the vibrational energy of the target sample molecule. Although vibrational Raman scattering is the most commonly studied form, rotational and electronic Raman scattering are also possible. The vibrational energy levels of a molecule are dictated by the masses and other properties of the constituent atoms, bond strengths, hydrogen bonding and inter-molecular interactions, molecular geometry, and the chemical environment. The spacing between the vibrational energy levels of the sample molecule is equal to the difference between the energy of the incident photon and the Raman scattered photon.

A Raman spectrum is a plot of the intensity of the Raman scattered light as a function of the difference in energy (frequency) between the incident radiation and the Raman scattered radiation. The difference in frequency between the incident and Raman radiation is independent of the frequency of the incident radiation.

Accordingly, Raman interaction involves the coupling between pump (incident), Stokes, and anti-Stokes radiation mediated by optical phonons in a Raman-active medium. In spontaneous Raman scattering, a pump beam with frequency $\omega_P$ traveling through a Raman medium scatters off of atomic or molecular vibrations and/or rotations, which are oscillating at frequency $\omega_V$. This scattering process creates a small amount of optical radiation at the new frequencies $\omega_S = \omega_P - \omega_V$ and $\omega_{aS} = \omega_P + \omega_V$ representing the Stokes and anti-Stokes frequencies, respectively.

In the spontaneous situation, the amount of radiation scattered into the anti-Stokes mode is much smaller than that scattered into the Stokes mode because at equilibrium, most of the population occupies the lowest vibrational level. The Stokes radiation is also much weaker than the pump (typically their relative intensities are $10^{-6}$ if the interaction length is 1 cm.) However, the intensity of the scattered Stokes radiation can be greatly enhanced if the interaction is stimulated by some initial injection of radiation at the Stokes frequency. In this stimulated Raman scattering (SRS) process, a sizable fraction of the pump radiation can be converted to the Stokes mode. In the general case, the field amplitudes of the Stokes and anti-Stokes modes obey the following coupled differential equations:

$$\frac{dA_S}{dz} = -\alpha_S A_S + \kappa_S A_{aS}^* e^{i\Delta kz}$$

$$\frac{dA_{aS}}{dz} = -\alpha_{aS} A_{aS} + \kappa_{aS} A_S^* e^{i\Delta kz},$$

where $A_S$ and $A_{aS}$ are the slowly-varying amplitudes of the Stokes and anti-Stokes waves, $\alpha_S$ and $\alpha_{aS}$ are the gain/non-linear absorption coefficients (on Raman resonance, $\alpha_S<0$ and $\alpha_{aS}>0$), $\kappa_S$ and $\kappa_{aS}$ are the coupling coefficients between the modes, and $\Delta k$ is the wave vector mismatch between the pump, Stokes, and anti-Stokes waves. If $\Delta k$ is large, phase matching does not occur and the Stokes and anti-Stokes amplitudes are decoupled from one another. In this case, the Stokes wave experiences gain, and the anti-Stokes wave experiences loss. This case is referred to as stimulated Raman scattering (SRS). If $\Delta k=0$, the modes are coupled and appreciable amounts of Stokes and anti-Stokes radiation can be created. In this situation, a Stokes seed causes radiation to be scattered into the anti-Stokes mode through coherent anti-Stokes Raman scattering (CARS) and an anti-Stokes seed causes radiation to be scattered into the Stokes mode through coherent Stokes Raman scattering (CSRS).

The typical Raman analysis instrument is composed of at least three parts: a light source, a scattered photon collector, and a spectrometer. The light source is typically a laser which generates a coherent beam of monochromatic light that can be used as a Raman pump. Furthermore, since laser radiation can be tightly focused onto a sample, a high degree of spatial resolution (i.e., microscopy) can be achieved in the analysis. The spatial resolution can be especially large for the intensity-dependent interactions of nonlinear Raman scattering because the interaction is strongest in the part of the beam which is most intense.

The scattered photons from the pump laser are collected by a photon collector. The collector typically may be designed to preferentially collect the Raman scattered light over the unwanted background signals, such as fluorescence. The collected Raman scatter is sent to the spectrometer. In conventional Raman spectroscopy (stimulated and spontaneous), the scattered light is typically analyzed by a grating-slit spectrometer. In this ubiquitous device, light is spatially separated into its spectral components by an optical grating and a slit scans across the separated components to determine the relative intensity of light at each frequency. The detector records the intensity of the Raman signal at each wavelength and plots the data as a Raman spectrum.

Unfortunately, since spectrometers usually require some type of mechanical scanning to sample the spectrum of the light, they have long acquisition times and require a continuous-wave or repetitive light source (i.e., they are unable to detect single ultra-fast pulses of optical radiation). Furthermore, the spectral resolution of the apparatus is typically related to the size of the spectrometer. Therefore, progressively larger, more expensive instruments are required to achieve greater spectral resolution, which prevents integration into microchip-scale electronics.

To perform fast acquisition, a multichannel array of photodetectors, often with post-detection amplifiers, may be used to simultaneously detect the entire spectrum. In this configuration, the system suffers from individual element mismatches, a problem that limits the dynamic range of the system. These mismatches are particularly difficult to calibrate when fast single-shot detection is desired. Specifically, the large RF bandwidth required of the detection circuitry renders calibration very difficult. The problem is somewhat similar to the interchannel mismatch problem which limits the dynamic range of multi-channel A/D converters.

Accordingly, there is an increasing need for high throughput Raman instruments for screening rare cell types, biomolecules, unknowns and chemical compounds with minimal sample preparation. There is a further need for miniaturized Raman spectrometers and instruments that have single-shot measurement capability. Such devices can be used, for example, in situations where continuous exposure to high intensity light could destroy the sample. There is also a need for a Raman spectrometer that is less sensitive to fluorescence that can normally mask the weaker Raman signals. The present invention meets these needs as well as others and is a significant improvement over the art.

BRIEF SUMMARY OF THE INVENTION

The present invention is an apparatus and method of measuring stimulated Raman scattering (SRS), coherent anti-Stokes Raman scattering (CARS), coherent Stokes Raman scattering (CSRS), and other Raman-type spectra of atomic, molecular, and crystalline species. The method utilizes dispersion to convert an optical spectrum into a waveform which can be detected directly in the time domain without the use of a conventional spectrometer. In the case of stimulated Raman spectroscopy, for example, the method exposes a sample to a pulsed probe beam and a Raman pump beam and the resulting Raman spectra is chirped, detected by an optical detector in the time domain, and analyzed. Alternatively, the pulsed probe may be chirped prior to incidence on the sample or both before and after stimulated scattering from the sample has occurred. In the preferred embodiment, the optical detector converts the Raman spectra into to an electronic signal that can be amplified and processed. The all-electronic spectrum analyzer eliminates the need for a traditional optical spectrometer.

Additionally, the apparatus and method provides a built-in rejection of fluorescence that normally can mask the weaker Raman signals. It can also be used to capture the Raman spectrum of a single molecule as it evolves. These features make it especially useful for analyzing samples in applications requiring high throughput, in applications where continuous exposure could destroy the sample, in applications where the chemical/physical state of the sample is rapidly and irreversibly evolving, and in applications where the physical size of a traditional optical spectrometer cannot be accommodated. It is also a particularly useful tool for identification of unknown samples, as well as detection of chemical compounds, biomolecules, and rare cell types (e.g., cancer cells) with minimal sample preparation. This technique is also extremely versatile because it is not anchored to any specific visible, infrared, or ultraviolet wavelengths.

According to one aspect of the invention, an apparatus and method are provided that allow a single-shot "snapshot" of a Raman spectrum to be measured in the time domain. The single-shot capability of the invention can be used to study chemical reactions directly in the time domain, without the need for repetitive analysis. This capability may be needed, for example, when the sample volume is small or when the chemical reaction under study is irreversible (i.e., to study the temporal evolution of a chemical species participating in an irreversible reaction). In these situations, it may not be possible to run the reaction repetitively or measure the spectra of the molecules at any one moment in time with conventional pump-probe spectroscopic methods, which require repetitive-waveforms and rely on temporal reconstruction.

The apparatus and methods of the present invention can be used to acquire spectral snapshots of the reaction at specific time intervals, using a single pump-probe pulse pair for each snapshot. Since both the snapshot frequency (determined by the pulse repetition rate) and the effective shutter speed (determined by the temporal width of the probe pulse) can be extremely fast, it is possible to study the temporal dynamics of ultra-fast reactions directly.

These techniques can also be used in combination with tip-enhanced Raman microscopy to study the dynamics of single molecules with single-shot temporal resolution. According to another aspect of the invention, the single-shot capability of the invention combined with the ultra-high resolution of Raman and tip-enhanced Raman microscopy allows microscopic spatio-temporal imaging. Since a Raman spectrum of each spatial domain can be acquired with a single pump-probe shot, a complete image of the sample can be formed by sweeping the lasers across the sample (or vice versa) at extremely high speed. Because each complete spatial scan can be completed relatively quickly, the image represents a snapshot of the complete sample in time (with a temporal resolution determined by the time it takes to make a complete scan). Thus, the image consists of two spatial dimensions plus the time dimension (a three-dimensional image). This technique can be performed in all three spatial dimensions with time resolution. For example, with three spatial dimensions plus time, provides 4D imaging.

According to another aspect of the invention, an apparatus and method is provided that allows sensing and detection of biochemical molecules using the high-resolution, single-shot capabilities of the invention. Matched detection techniques can be incorporated in order to increase detection efficiency and effectiveness. Furthermore, practical implementations of the invention should be relatively low cost, making widespread deployment of these bio-detectors feasible.

Another aspect of the invention is to provide an apparatus and method for high throughput screening of cancer and other rare cell types, and biochemical sensing and combinatorial chemistry with high throughput and matched detection.

A further aspect of the invention is to provide an apparatus utilizing Raman post-amplification and incoherently-pumped Raman post-amplification of spectroscopic signals.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWINGS

The invention will be more fully understood by reference to the following drawings which are for illustrative purposes only.

DETAILED DESCRIPTION OF THE INVENTION

Referring more specifically to the drawings, for illustrative purposes the present invention is embodied in the apparatus and method generally shown in FIG. 1 through FIG. 10. It will be appreciated that the apparatus may vary as to configuration and as to the details of the parts, and that the methods may vary as to the specific steps and sequence, without departing from the basic concepts as disclosed herein.

Figure 1:
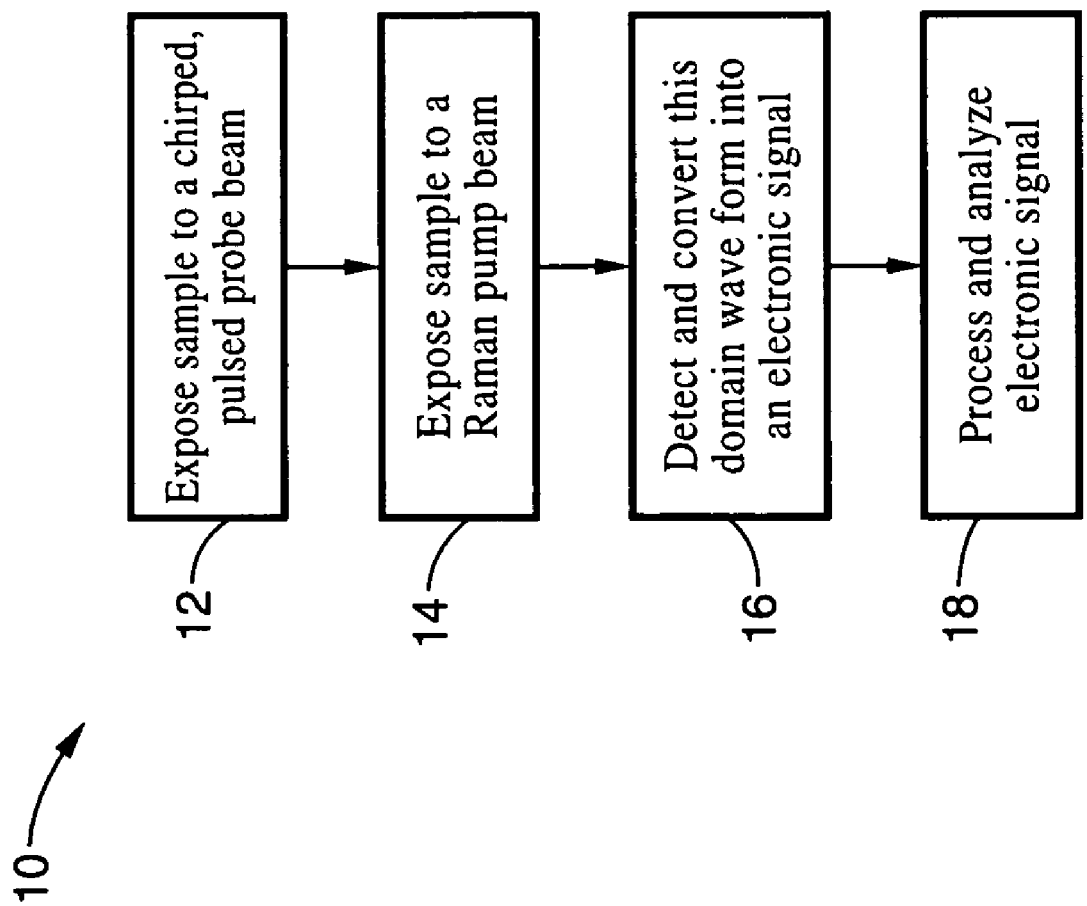
FIG. 1 is a flow chart of one embodiment of the method for Raman spectroscopy according to the present invention.

Turning first to FIG. 1 a block diagram of one of the methods of the invention is shown. Although a method 10 for stimulated Raman spectroscopy is shown in FIG. 1, the method and apparatus can be adapted to other Raman-based spectroscopic techniques such as coherent anti-Stokes Raman scattering (CARS), coherent Stokes Raman scattering (CSRS), spontaneous Raman scattering and others. In the embodiment shown in FIG. 1, a sample is exposed to a chirped broadband pulse at Block 12 and an intense, preferably narrow-band, Raman pump pulse at Block 14. The resulting Raman spectra is detected at Block 16 and preferably converted to an electronic signal that can be processed and analyzed at Block 18. The Raman spectrum scattered from the sample is mapped into a time-domain waveform.

At Block 12, a sample is exposed to at least one probe beam of chirped, pulsed light. The source of light is preferably a supercontinuum that is directed through a temporally dispersive element such as an optical grating, optical fiber, chirped mirror or fiber Bragg grating, prism, etc. Alternatively, a direct source of chirped light may be used. The probe pulse may be optically amplified and filtered prior to dispersion. The probe wavelengths or ranges of wavelengths should be selected to include the Raman resonance frequencies of the sample under investigation given the particular pump wavelength. The constituent frequencies of the chirped, pulsed probe beam are temporally distributed in a way that allows the Raman scattered light from the sample to be mapped into a time-domain waveform. Alternatively, the same result may be accomplished by chirping the light after it has been scattered by the sample. This method may be advantageous, for example, in situations where it is desired that the probe pulse be temporally short during the scattering process for better time resolution. Another factor that may be considered in this context is the temporal width of the pump pulse. In order for the pump to stimulate Raman scattering uniformly across the probe, the pump should have a longer duration than the probe pulse. Thus, in situations where the pump pulse is fairly short, for example if its width is on the order of tens of picoseconds or less, it will generally be necessary to use a temporally short probe and to chirp the probe pulse after the scattering process so that the probe pulse remains shorter in time than the pump during the scattering.

In one embodiment of the invention, wavelengths or ranges of wavelengths of the probe beam have specially prepared amplitudes for the purpose of performing stimulated matched detection of an unknown chemical species or other constituents in the sample.

At Block 14, a Raman pump beam is directed to the sample at approximately the same place and time as the probe beam. The Raman pump beam is preferably narrow-band or monochromatic laser light. It is desirable to use a narrow band or monochromatic pump because the spectral width of the pump determines the limit of the frequency resolution of the measurement. In some situations, a broader bandwidth pump may be required, sacrificing some frequency resolution, in order to produce a short enough pump pulse to achieve the power levels to generate sufficient stimulated Raman gain. The pump must achieve a power level that will generate sufficient Raman gain for optimal recording of the Raman spectrum of the sample. Although a single pump beam is shown at Block 14, the sample may be exposed to more than one pump beam. The Raman pump laser may be pulsed or continuous wave.

Although two lasers are described at Block 12 and Block 14, it will be understood that the probe and pump pulses can be derived from the same light source by splitting, filtering, amplifying, and delaying portions of its output radiation as necessary.

Exposing the sample to the combined chirped probe beam and the Raman pump beam creates a Raman spectrum of light that is scattered from the sample. In other words, the stimulated Raman gain spectrum of the sample is encoded onto the probe beam in the scattering process. The intensity of the Raman signal is normally proportional to the intensity of the incident light and scattering also generally becomes more efficient at shorter wavelengths. Accordingly, the intensity and operating wavelength of the incident beams can be optimized and tailored to the assay.

At Block 16, the resulting Raman spectra are detected by an optical detector that preferably converts the optical signal to an electrical signal. Each probe pulse provides a "snapshot" of the Raman spectrum at a point in time.

In conventional Raman spectrometers, the scattered frequency components are analyzed by separating them in space. In contrast, in the present invention, the frequencies of the Raman spectrum are separated and detected in time. Time mapping of the Raman spectrum will occur without significant interference from background radiation or background fluorescence. In one embodiment of the invention, the Raman spectrum may be optically amplified prior to detection. One method for optically amplifying the signal utilizes Raman amplification. This Raman amplification can be implemented, for example, as distributed amplification (i.e., amplification throughout a distributed medium) directly in the dispersive medium placed after the sample. In this way, the signal is simultaneously amplified and dispersed for time-domain detection. As a result, the dispersive element can have lower loss, can be transparent, or can even have net gain. The advantage of utilizing this Raman amplification over other types of optical amplification is that Raman amplifiers are not fundamentally restricted to particular wavelengths or bands, but can operate wherever suitable pump sources and Raman media are available. Utilizing distributed amplification rather than discrete optical amplification has the further advantage that the signal is always maintained at a fairly uniform level and never reaches very low levels where noise becomes more significant or very high levels where optical nonlinearities can lead to distortion.

In order to implement this distributed Raman amplification, Raman pump light must be introduced into the dispersive medium along with the signal. If the signal to be amplified is broadband and the pump sources are monochromatic, multiple pump lasers may be required to produce uniform gain across the signal. In many practical situations, however, broadband, incoherent light may serve as an adequate pump. Intense, broadband amplified spontaneous emission (ASE) can be intentionally produced by conventional gain media for this application. The advantage of this approach is that fewer ASE sources are necessary to provide a flat gain spectrum across the signal bandwidth. Although the noise of the ASE will be transferred to the signal during the amplification process, this additional noise will not have a significant impact if the limiting noise contribution in the measurement process comes from the detector and/or electronic digitizer. In this case, increasing the amplitude of the signal may facilitate its detection even if the relative noise level in the signal increases.

One or more optical detectors preferably convert the time-domain waveform into an electronic signal that can be electronically filtered, amplified, and processed if necessary at Block 18. The optical detector can also be a coherent optical detector that generates a signal from which the phase of the time-domain waveform can be recovered. The coherent optical detector can be an optical mixer, an interferometer, or a frequency-resolved optical gating instrument or comparable device.

At Block 18, the electronic signal is processed and analyzed. The electronic signal may be digitized and then electronically processed, stored, or displayed. In order for the signal to be captured by an electronic digitizer or oscilloscope, the time-domain waveform should lie within the bandwidth of the instrument. Furthermore, there should be enough sampling points per unit time for the waveform to be accurately represented. Therefore, the dispersion used to map the spectrum into a time-domain waveform must be sufficient to stretch the waveform enough to be captured by the digitizer. In addition, if single-shot data acquisition is desired, the digitizer must be capable of acquiring the necessary number of sampling points in a single-shot measurement.

Once the signal has been digitized, electronic signal processing may be used to remove the deleterious spectral non-uniformities or non-idealities of the beams from the electronic signal. Composites of the acquired "snapshots" may be created in two or three dimensions or as a sequence of movie frames and displayed with the assistance of software and a computer. The acquired signals may also be compared with a library of known signals as part of the analysis. For example, the digitized electrical signal may be electronically cross-correlated with the known Raman spectrum of one or more chemicals or materials for the purpose of matched detection of unknown chemical species or other constituents in the sample under analysis.

Figure 2:
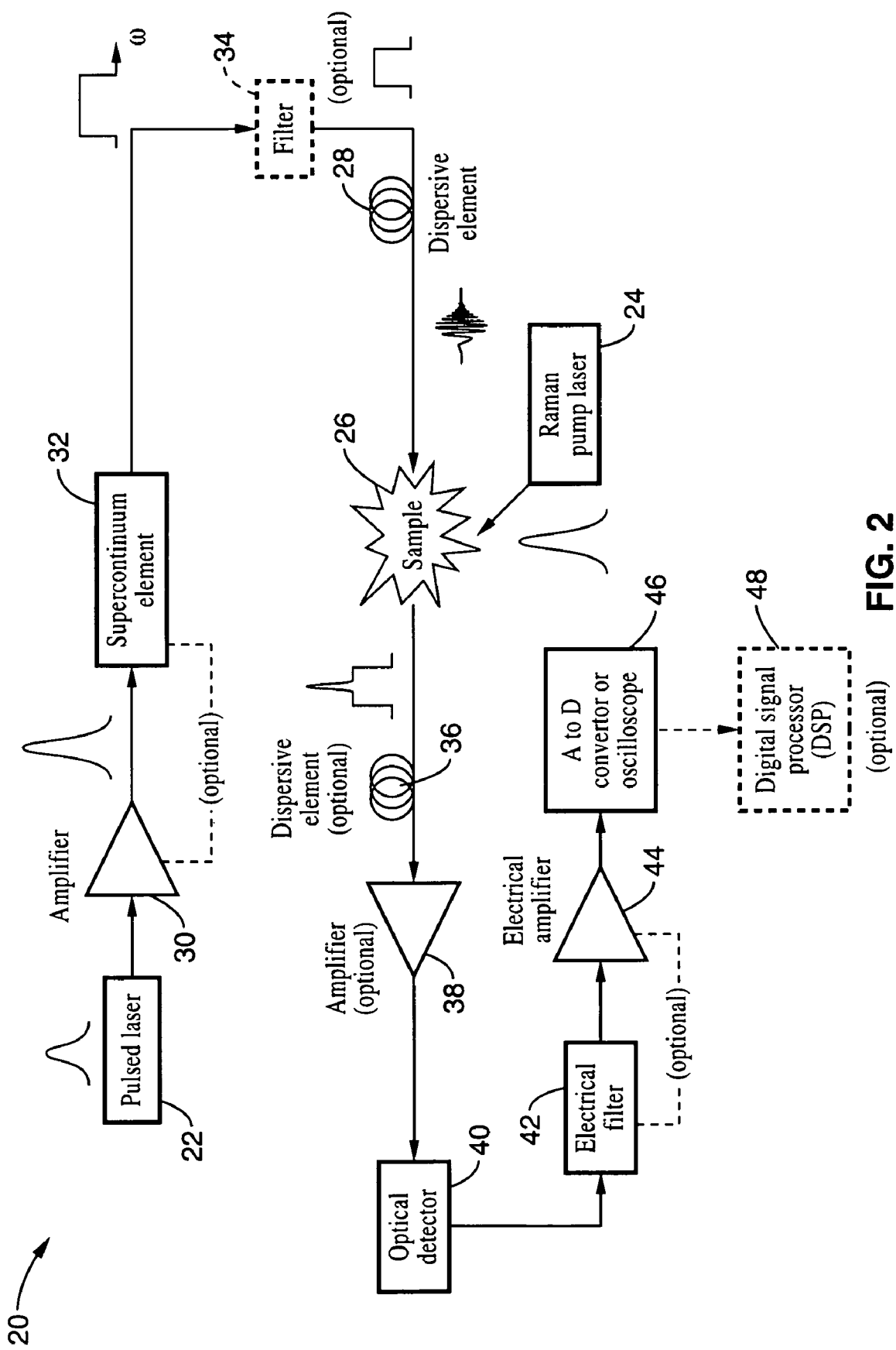
FIG. 2 is a schematic block diagram of one embodiment of the chirped wavelength encoding and electronic time-domain sampling apparatus according to the present invention.

Referring now to FIG. 2, a schematic diagram of one embodiment of the apparatus 20 is shown in general form. A pulsed probe laser 22 and a Raman pump laser 24 are directed to a sample 26 and light scattered from the sample 26 is mapped into a time-domain waveform, detected, and analyzed. The output from the pulsed probe laser 22 is chirped or dispersed with a temporally dispersive element 28 prior to being directed on the sample 26. Alternatively, either this temporally dispersive element 28 or a second dispersive element 36 may be placed after the light is scattered by the sample 26. Although a single pulsed probe laser and a single pump laser are shown, it will be understood that more than one pump and probe laser or supercontinuum and varying frequencies may be used.

In the embodiment shown in FIG. 2, an optical amplifier 30 amplifies an optical pulse from the pulsed laser 22, which is used to pump a supercontinuum generator 32. The optional amplifier 30 may not be required if the initial laser 22 pulse is already powerful enough to generate the supercontinuum. Also, if the initial pulse has a very large bandwidth, the amplifier 30 and/or the supercontinuum generator 32 may not be necessary. For example, titanium:sapphire (Ti:S) mode-locked lasers can generate ultra-fast pulses (<10 fs) with extremely large bandwidth (>100 nm).

Next, the supercontinuum of radiation may be passed through an optional bandpass filter 34 and sent through a dispersive element 28, which imparts a frequency chirp to the probe pulse from the probe laser 22. The chirp, which may be seen as representing a code, may be a linear or a more complex function. The chirped pulse is directed to a selected point on a sample 26 as the Raman probe (Stokes seed).

A pulse from a second laser, the Raman pump laser 24, is also directed onto the sample 26 at a selected point so that the pump and probe pulses overlap on the sample in time and space. The Raman pump laser 24 and the probe laser 22 may be derived from a single laser source. Precise temporal and spatial overlap of the pulses from the pump laser 24 and the probe laser 22 may not be required depending on the characteristics of the sample 26. In addition, the relative delay, pulse shapes, and spatial overlap of the two pulses can be controlled for the purposes of enhancing the operation of the present invention.

The pump and probe pulses directed to the sample 26 stimulate Raman scattering if they are Raman resonant with the sample. Moreover, if the probe laser 22 bandwidth is large enough, many Raman lines of the sample may be simultaneously excited with a single pair of pump and probe pulses. In the frequency domain, the stimulated Raman spectrum appears on top of the spectrum of the chirped continuum.

The radiation that is scattered may be passed through an optional second dispersive element 36, which can either provide additional dispersion of the same sign as the first dispersive element, or an opposite temporal dispersion. If opposite dispersion is added, this will tend to counteract the effect of the first dispersive element 28. However, if less dispersion is provided in the second element 36, there will still be net dispersion from the two dispersive elements 28, 36. This partial dispersion cancellation technique can be used if one wishes to initially disperse either pulse more than necessary so as to avoid subjecting the sample 26 to high peak power levels.

In the embodiment shown in FIG. 2, the second dispersive element 36 may be used alone or at the same time as dispersive element 28. In many situations it may be desirable to use only the second dispersive element 36 to chirp the light after it has been scattered from the sample, without the use of the first dispersive element 28. When the second dispersive element 36 is used alone, the spontaneous Raman emissions from the sample 26 due to the pump light can also be chirped and subsequently detected.

After traversing the optional second dispersive element 36, the pulse may be amplified by an optional amplifier 38 and is then detected by an optical detector 40. The optional amplifier 38 may also represent a distributed Raman amplifier, which may be implemented to amplify the signal as it propagates through the second dispersive element 36. The detector 40 is preferably an optical detector, such as an avalanche photodiode, that can convert the photons scattered from the sample 26 or received by amplifier 38 to an electronic signal.

Next, the electrical signal from the optical detector 40 may be filtered to limit its bandwidth by the optional electronic filter 42 and optionally amplified by an electrical amplifier 44. Limiting the bandwidth to no more than is necessary reduces the noise in the subsequent analog to digital conversion. The signal may then be either digitized by an analog to digital converter (A to D converter) 46 or displayed on an oscilloscope. The signal may also be processed or analyzed with a digital signal processor 48 or computer and displayed and stored.

Since the Stokes seed pulse was chirped by the first dispersive element 28 and/or the scattered signal is chirped by the second dispersive element 36, the stimulated Raman spectrum is mapped into the time domain. In particular, the different frequencies in the scattered probe spectrum arrive at the detector at different times. As a result, the spectrum can be sampled in the time domain by the Analog to Digital converter 46 or displayed directly on an analog oscilloscope without the need for a spectrum analyzer.

In addition, since background radiation (e.g., fluorescence) emitted by the sample is not chirped when the second dispersive element 36 is absent, fluorescence does not appear as part of the stimulated Raman spectrum that is measured in the time domain. Furthermore, since the Raman spectrum can be measured with a single set of pump and probe pulses, the technique has a single-shot capability.

The apparatus and methods can also be used for spontaneous Raman spectroscopy if the probe pulse 22 is eliminated as indicated previously. In this situation, the pump 24 excites spontaneous Raman scattering in the sample 28, and this spontaneous emission is then temporally dispersed (chirped) by the dispersive element 36. Then, the chirped spontaneous emission can be sampled in the time domain as previously described. Since spontaneous Raman scattering is typically a much weaker effect compared with stimulated scattering, the spontaneous signals will generally be smaller than those obtained with the stimulated Raman option.

It can be seen that the apparatus and method can be implemented over a large range of possible pump and probe wavelength bands. For example, probe pulses and high peak power pump pulses could be produced using a telecommunications laser (e.g., an erbium-doped fiber laser or diode laser) and/or amplifier operating between 1300 and 1600 nm. It is also possible to frequency double (second harmonic generation) or triple (third harmonic generation) a telecommunications laser to produce higher frequencies for use in the apparatus. Another type of laser that could be used is the titanium:sapphire laser, which offers short, high-power pulses at wavelengths between 650 and 1100 nm, usually in the vicinity of 800 nm. Neodymium-doped yttrium aluminum garnet lasers and ytterbium-doped fiber lasers may also be used to produce the required optical radiation. Although these laser types are explicitly mentioned herein, other types of laser sources may also be used.

Figure 3:
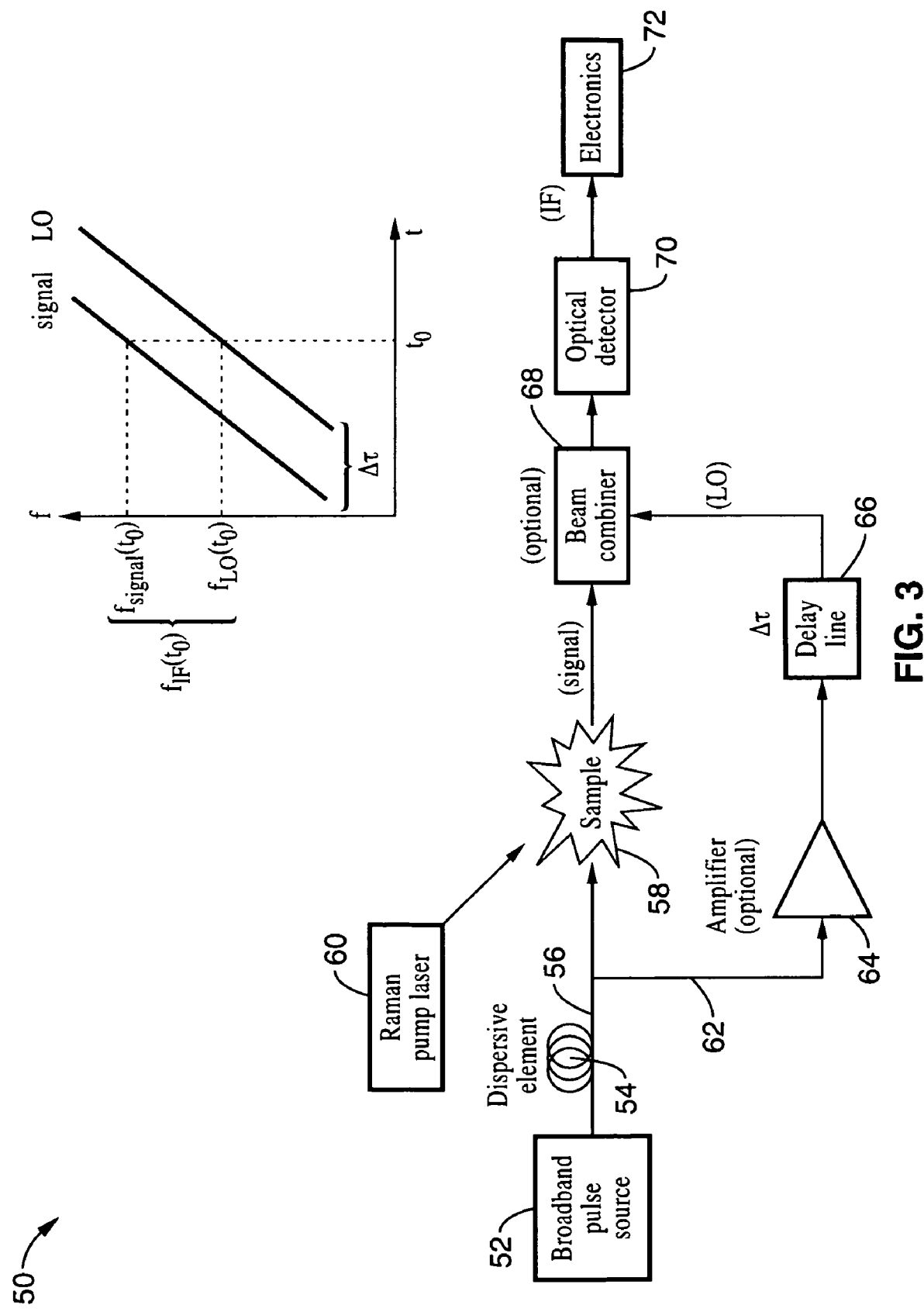
FIG. 3 is a schematic block diagram of an alternative embodiment of the chirped wavelength encoding and electronic time-domain sampling apparatus of FIG. 2 with coherent detection using a chirped local oscillator pulse and relative delay.

In addition to providing the magnitude of the Raman spectrum, the apparatus and methods can also provide the phase information. Referring also to FIG. 3, coherent optical detection is performed in the illustrated mode of operation 50. In the embodiment shown in FIG. 3, the probe beam 56 is provided by a broadband pulsed laser 52 with a dispersive element 54 to generate a chirped, pulsed probe beam 56 directed to sample 58. A Raman pump beam 60 is also directed to sample 58.

Coherent detection can be achieved, for example, by mixing the probe beam with a local oscillator (LO) at the photodetector. This type of coherent detection is well known and has been used in optical communication. The local oscillator (LO) may be a copy of the chirped supercontinuum, or an independent pulse or a continuous-wave beam. If, for example, the LO is a copy of the chirped supercontinuum, the relative time delay between the LO and the probe will determine the intermediate frequency (IF) of the mixer.

In the embodiment shown in FIG. 3, the Stokes continuum probe pulse is split into two parts prior to incidence with the sample. One part of the beam 56 is sent through to the sample. The second part of the beam 62 is sent through another path, containing an optional amplifier 64 and an optional delay line 66. The amplifier 64 amplifies the LO in order to increase the detection sensitivity of the signal and the delay line 66 adds a time delay $\Delta\tau$ to the LO pulse. The two pulses are subsequently recombined with a beam combiner 68 (optional if the two beams can be directly interfered on the optical detector) and detected with an optical detector, such as a photodiode. The detector 70 generates an intermediate frequency (IF) electronic signal from the mixing of the signal and LO pulses. This electronic signal is then (electronically) processed and analyzed with electronics 72. The frequency of the IF electronic signal at a point in time $t_0$ is given by the difference between the signal from the sample and the local oscillator frequencies at that time:

$f_{IF}(t_0) = f_{signal}(t_0) - f_{LO}(t_0)$.

Another alternative to the use of a mixer for coherent detection is the Frequency-Resolved Optical Gating (FROG) technique, a method that is also capable of recovering the phase of an optical waveform. Also, standard interferometric techniques may be used to measure the phase of the Raman signal relative to that of a known reference waveform.

Accordingly, the use of an optical chirp, an opto-electronic detector, and analog to digital converter (or oscilloscope) in the instrument eliminates the need for a bulky spectrometer in Raman spectroscopy. There is no mechanical scanning of any kind in the apparatus, which allows for extremely rapid analysis. Furthermore, the detection of the entire spectrum can be accomplished with a single fast opto-electronic converter channel. The converter can be a p-i-n photodiode, an avalanche photodiode (APD), a photomultiplier tube (PMT), or a different type of opto-electronic detector.

Each supercontinuum Stokes pulse provides a snapshot of the Raman spectrum that is sampled in time (i.e., neither repetitive waveforms nor static samples are required). This feature is particularly useful for studying samples undergoing rapid, transient processes or in applications where high throughput is required. For each supercontinuum pulse, a Raman spectral "snapshot" can be recorded from the sample. For example, with megahertz (MHz) pulse repetition rates, more than one snapshot per microsecond is possible. The effective "shutter speed" (i.e., the temporal resolution) of each spectral snapshot is determined by the temporal width of the supercontinuum probe.

Figure 4:
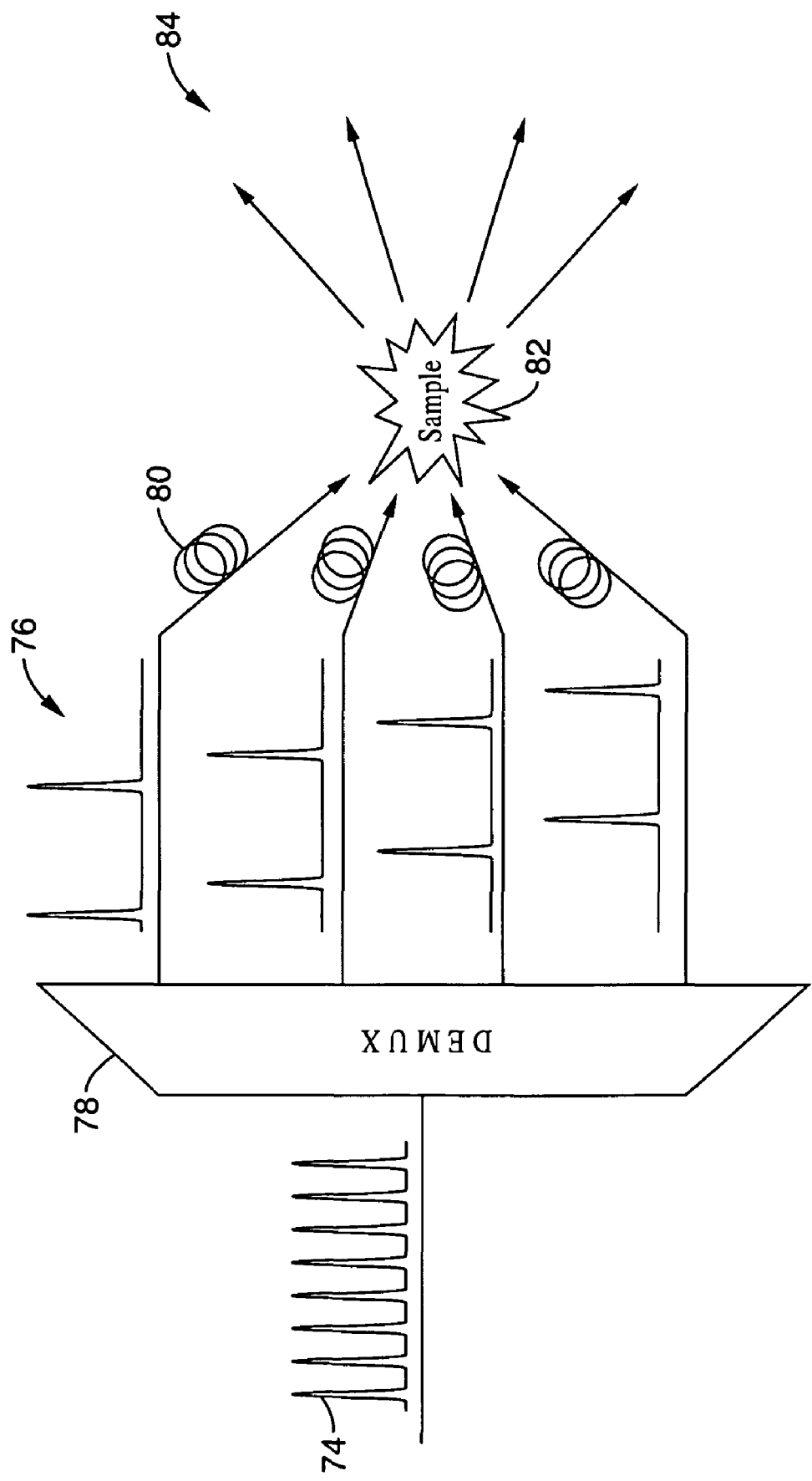
FIG. 4 is a schematic block diagram of an alternative embodiment of the chirped wavelength encoding and electronic time-domain sampling apparatus according to the present invention with time-division multiplexing of the probe pulse prior to dispersion.

Turning now to FIG. 4, the elimination of the conventional spectrometer and the use of ultra-fast pulse repetition frequencies will allow the generation of very high "snapshot" frequencies. In some cases, however, an additional step may be necessary in order to handle ultra-high repetition rates. Time-division multiplexing (TDM), such as terabit per second (Tb/sec) TDM, may be used to accommodate the speed. If ultra-high pulse repetition rates are employed, there is a limit to how much the spectrum of each pulse can be dispersed before successive pulses overlap with one another. However, time division multiplexing allows a rapid pulse train 74 to be separated into trains 76 with lower repetition rates with the use of a demultiplexer 78 as shown schematically in FIG. 4. The separated pulse trains 76 can be independently dispersed with dispersion elements 80 and directed to a sample 82 and the resulting Raman spectra 84 can be analyzed. For example, terahertz (THz) pulse repetition rates allow for the snapshot interval to be less than one picosecond, which would facilitate single-shot monitoring of chemical and biological reactions on very short timescales. Alternatively, a rapid pulse train may be dispersed after it scatters from the sample instead of before the scattering process. In this case, the demultiplexer 78 may be used after the scattering has occurred and prior to the dispersion.

Figure 5:
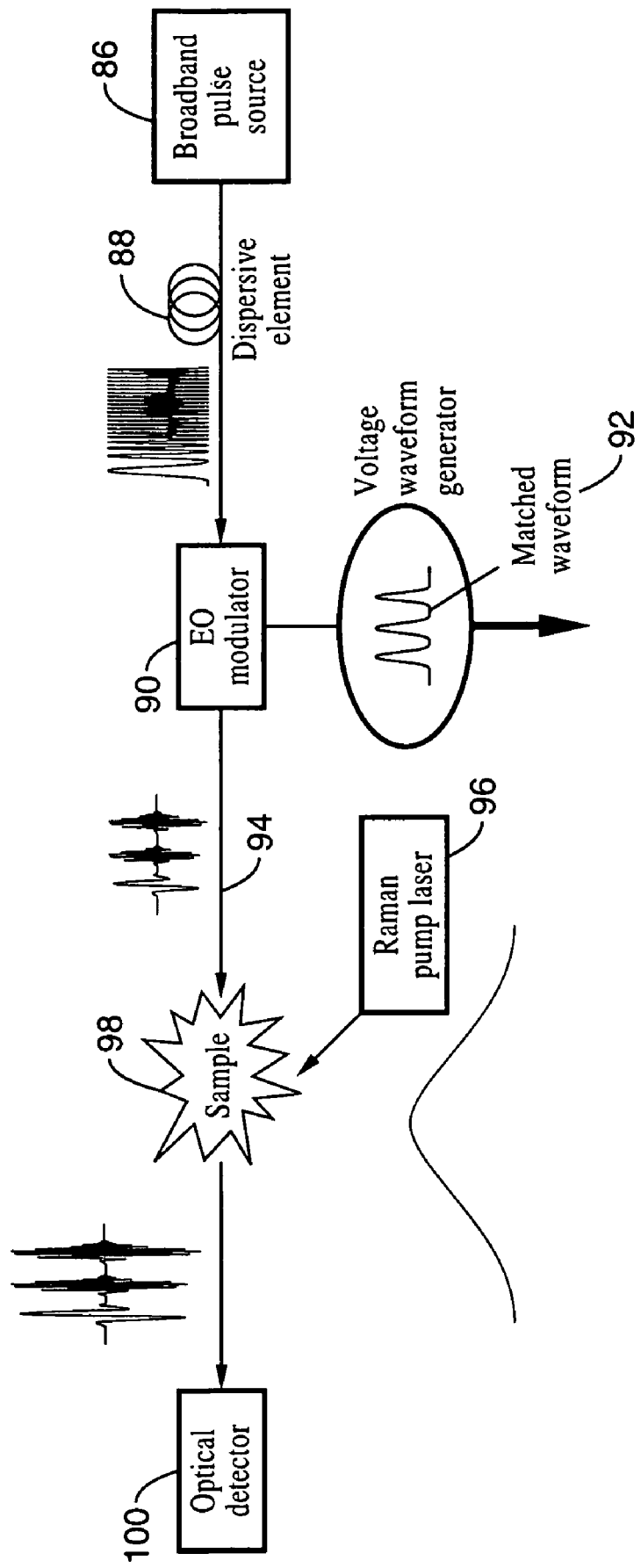
FIG. 5 is a schematic block diagram of an alternative embodiment of the chirped wavelength encoding and electronic time-domain sampling apparatus of FIG. 2 with stimulated matched detection using an electro-optic modulator.

Referring now to FIG. 5, an embodiment of the invention adapted to conduct cross-correlation matched detection is shown. Matched detection of a substance utilizes cross correlation with spectral libraries to identify chemical species. Substances can be identified by numerically performing cross correlations of the acquired spectral data with known spectral information of different chemical compounds. For example, it can be determined whether an unknown organic liquid contains benzene by measuring the spectrum of the unknown and computing the cross correlation with the known spectrum of benzene contained in a spectral library. If the unknown contains benzene, a significant cross-correlation signal will be observed or if it does not contain benzene the cross correlation will be small. The technique can be applied to more complicated situations with a greater number of possible substances in the unknown mixture. Accordingly, Raman spectroscopy measured by chirped wavelength encoding and electronic time-domain sampling can be used to rapidly identify unknowns.

Alternatively, instead of numerically computing a cross correlation after the spectral data has been collected, a Stokes supercontinuum seed with a spectrum matching that of a particular substance from the spectral library can be prepared. If this substance is present in the unknown sample, then a much larger stimulated signal will be obtained than a non-specific Stokes seed is used. Thus, we can create a sensitive detector for a particular substance or group of substances.

An example of one embodiment of stimulated Raman matched detection is shown in FIG. 5. A broadband pulse from a laser or supercontinuum 86 is dispersed with a dispersive element 88 and then modulated by an optical modulator 90 (e.g., an electro-optic (EO) modulator) using a voltage waveform 92 matching the spectrum of the species desired to be detected. As a result, the amplitude of the supercontinuum pulse 94 is modified to match this spectrum. A Raman pump pulse from a Raman pump laser 96 is directed to the sample 98 with the modulated probe pulse 94. When the modulated probe pulse 94 is incident on the sample 98, there will be more significant stimulated Raman scattering detected by optical detector 100 if the sample contains the species matching the spectrum imposed on the continuum. On the other hand, weaker scattering will result if this species is not present in the sample.

Stimulated matched detection (SMD) described above will facilitate high throughput and single-shot detection. Shaping the spectrum via time-domain modulation by an electro-optic modulator offers the ability to change the probe spectrum on a very short timescale resulting in extremely rapid scanning through a large number of waveforms 92. Because traditional optical filters cannot be tuned very rapidly (the tuning rate is typically limited to kHz), this ultra-fast analysis of the spectrum is not available in the prior art.

Figure 7:
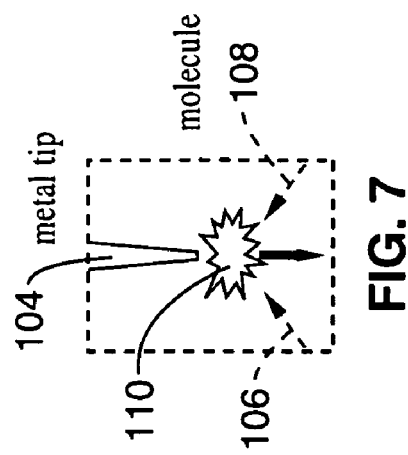
FIG. 7 is a detailed section of the schematic diagram of tip-enhanced Raman microscope of FIG. 6.
Figure 6:
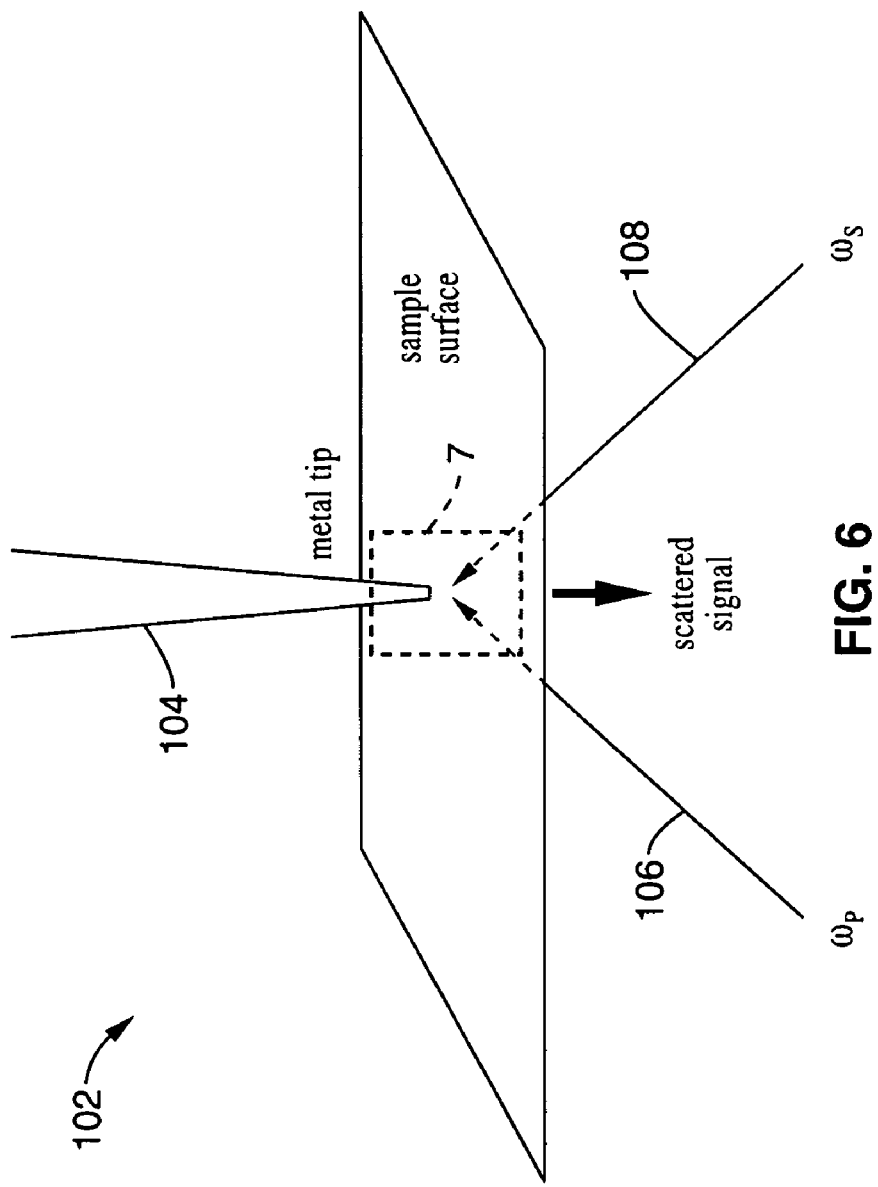
FIG. 6 is a schematic diagram of tip-enhanced Raman microscopy apparatus according to the present invention.
Figure 8:
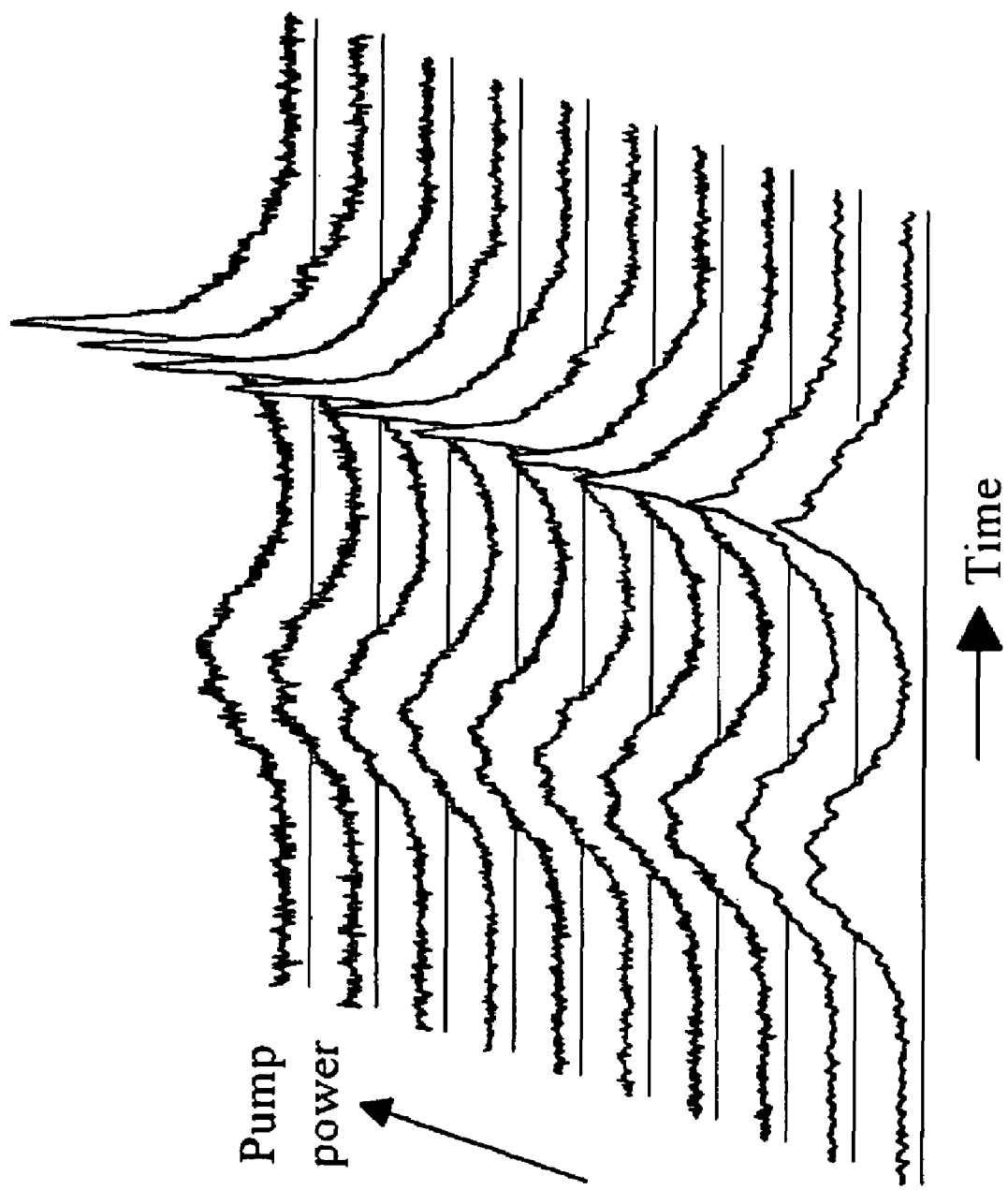
FIG. 8 are graphs of the stimulated Raman spectrum of a silicon waveguide at different pump power levels.

A schematic diagram of tip-enhanced Raman microscopy is shown in FIG. 6 and FIG. 7. Since stimulated Raman scattering is an intensity-dependent, nonlinear optical interaction, tightly focused beams can generate highly localized scattering events. In particular, only the most intense region of the spatial profile of the beam will generate a strong SRS (or other Raman-type) signal. This feature allows stimulated Raman imaging with significantly high, even sub-wavelength, resolution. If the sample is scanned using a piezo-controlled translation stage across the focal point, or conversely if the beams are swept across the sample (e.g., with an acousto-optic modulator), a high-resolution Raman image of the sample can be obtained. Moreover, the scanning can potentially be performed in all three dimensions, producing full three-dimensional (3D) images.

Furthermore, since chirped wavelength encoding and electronic time-domain sampling is a single-shot technique, the sample and/or beams can be scanned at a very high rate, allowing for extremely fast image acquisition times. In this way, spatio-temporal Raman snapshots of the sample can be obtained (three space dimensions+time=4D imaging).

In the diagram and details shown in FIG. 6 and FIG. 7, tip-enhanced Raman microscopy 102 is schematically shown. In the embodiment shown, a sharp metal tip 104 is placed in close proximity to or in direct contact with a surface to be studied. Two laser beams (pump and probe) are tightly focused onto the sample 110. When the pump 106 and probe 108 beams are directed to the surface at the contact point, the metal tip 104 produces a large enhancement of the electric field at that location. This enhancement is very localized, allowing for scattering from single molecules (i.e., resolution beyond the diffraction limit of light). Tip-enhanced Raman microscopy when combined with chirped wavelength encoding and electronic time-domain sampling can measure Raman and Raman-type spectra with single-shot excitation. This technique allows the study of molecular dynamics and chemical reactions to be directly probed and potentially controlled.

Furthermore, if the pump beam 106 and Stokes probe beams 108 are Raman resonant with each other and are phase matched, anti-Stokes radiation will be generated. The Stokes probe pulse 108 is intentionally frequency chirped for the purposes of detecting the scattered anti-Stokes signal in the time domain. Alternatively, if the Stokes light is not chirped, the anti-Stokes signal can be chirped for time-domain detection. Since this is an intensity-dependent, nonlinear optical interaction and the beams are tightly focused onto the sample, an anti-Stokes image of the sample can be generated with high spatial resolution by scanning the beams across the sample 110, for example. In a CARS process, the phase-matching can be chosen to generate a backscattered signal. For non-phase-matched Raman processes like SRS, the signal will typically be scattered along the direction of the Stokes seed. Therefore, experimental geometries different from that depicted in FIG. 6 and FIG. 7 may be required in some situations.

Accordingly, the single-shot capability of the invention combined with the ultra-high spatial resolution of Raman and tip-enhanced Raman microscopy allows microscopic spatio-temporal imaging. Since a Raman spectrum of each spatial domain can be acquired with a single pump-probe shot, a complete image of the sample can be formed by sweeping the lasers across the sample (or vice versa) at exceptionally high speed.

For example, sweeping the pump 106 and probe 108 beams across the sample 110 and rastering the focal point across every point in the domain will provide an image in two spatial dimensions. Each time a pump-probe pulse pair is incident on the sample 110, the focal point may be moved slightly in the two-dimensional plane. Since the nonlinear properties of stimulated Raman scattering make the spatial interaction highly localized, the spatial resolution can be extremely high. Tip-enhanced microscopy can further enhance the spatial resolution of the results. With many pump-probe pulse pairs, a high-resolution image of the sample can be created. Because each complete spatial scan can be completed relatively quickly, the image represents a snapshot of the complete sample in time (with a temporal resolution determined by the time it takes to complete the scan). Thus, the image consists of two spatial dimensions plus the time dimension (a three-dimensional image). This technique can be performed in all three spatial dimensions with time resolution. For example, with three spatial dimensions plus time will produce a 4D image.

It is also possible to enhance Raman scattering signals using colloidal metal nanoparticles. If nanometer-scale metal particles (e.g., gold, silver) are placed in a colloidal suspension in the Raman medium, a significant enhancement of the scattering cross-section may result. Furthermore, the plasmon resonances of the nanoparticles can also be used to alter the Stokes/anti-Stokes ratio in Raman scattering. Nanoparticle-enhanced Raman spectroscopy can be used in combination with chirped wavelength encoding and electronic time-domain sampling to provide single-shot, background-free Raman and Raman-type spectral data.

Another significant capability of the apparatus and methods is that fluorescence associated with the sample can be automatically eliminated. Since the Raman signal is chirped in the apparatus and methods of the present invention, unwanted background signals (e.g., fluorescence) can be automatically distinguished from the Raman spectrum. Specifically, in the absence of the second dispersive element shown in FIG. 2, the fluorescence generated by the Raman medium will not be chirped and thus will appear as a constant background in the time domain. The Stokes spectrum can also be can be encoded on the continuum (in the time domain) at the pulse rate to enhance the detection sensitivity and hence selectivity while providing fast throughput. Fluorescence rejection facilitates SRS measurements, whereas, usually CARS or FSRS must be used to eliminate fluorescence. SRS has advantages over CARS in certain situations because SRS does not need to be phase matched and SRS spectra are typically easier to interpret than CARS spectra.

The invention may be better understood with reference to the accompanying examples, which are intended for purposes of illustration only and should not be construed as in any sense limiting the scope of the present invention as defined in the claims appended hereto.

Example 1

To illustrate the invention, the embodiment shown schematically in FIG. 2 was constructed using a silicon waveguide as a sample. Silicon was selected because the vibrational Raman spectrum of silicon has been well studied using standard techniques and stimulated Raman scattering in silicon has been employed to construct Raman lasers and amplifiers.

The master oscillator that was used to generate the pump and probe pulses was a mode-locked erbium-doped fiber laser producing near-transform-limited picosecond pulses at approximately 1550 nm with a repetition rate of 25 MHz. The pump pulses were generated by pre-stretching a fraction of the output pulses to approximately 50 ps and then amplifying in a large-mode-area erbium-doped fiber amplifier to a desired level.

A supercontinuum Stokes probe was generated directly within the gain fiber of a separate specialty erbium-doped fiber amplifier using a portion of the oscillator output as the seed. The supercontinuum pulses were band-pass filtered at ~1685 nm ($\Delta\lambda$=10 nm), synchronously combined with the pump pulses using a wavelength-division multiplexer (WDM), and coupled to a silicon waveguide. At the output of the waveguide, the pump light was removed using another WDM, leaving only the supercontinuum encoded with the stimulated Raman spectrum of silicon.

The encoded pulse was then stretched in a module of dispersion-compensating fiber (DCF). DCF is a commercial fiber designed to compensate for anomalous dispersion in long-haul optical fiber networks. This module produced approximately −1300 ps/nm of GVD with a measured loss of ~10 dB at the probe wavelength. The stretched pulses were then delivered to an amplified photodetector whose electrical output was captured by a real-time 20 gigasample-per-second oscilloscope. A delayed copy of the supercontinuum probe (not synchronized with the pump) was also routed through the waveguide as a reference.

Using a single detector, measurements of the stimulated Raman spectrum of silicon in real time for different pump power levels were taken. Representative Raman spectra can be seen in FIG. 8. One copy of the probe pulse was synchronized with the pump, and therefore experienced Raman gain, while the other copy was delayed and therefore passed through the silicon waveguide unaltered by Raman scattering.

Figure 9:
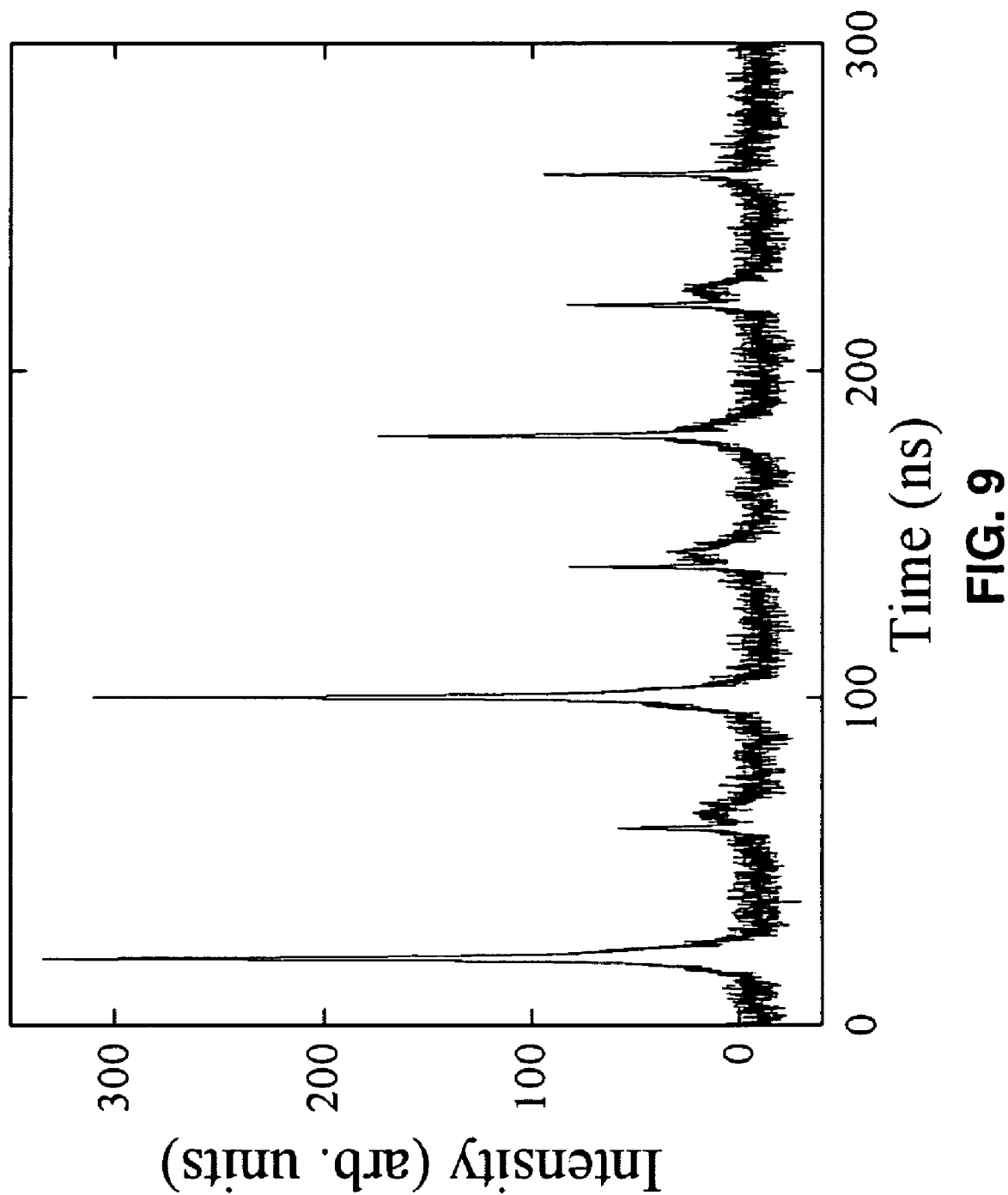
FIG. 9 is a graph of a non-repetitive signal generated by stimulated Raman scattering in a silicon waveguide sample using an unstable supercontinuum probe.

To illustrate the real-time capabilities of the methods, measurements of a time-varying signal using the apparatus described above and shown in FIG. 2 were taken but without the reference pulse. The time-varying signal was generated using an unstable supercontinuum probe. In particular, it was observed that if the supercontinuum pulse energy is increased above a threshold level, the amplitude becomes unstable and varies randomly from pulse to pulse. As seen in FIG. 9, this fluctuation was reflected in real-time SRS measurements utilizing the unstable supercontinuum pulses as the probe.

Although the Raman gain spectrum itself remained unchanged over time, the apparatus and methods captures transient effects and can be employed to monitor a dynamic Raman spectrum in real time, with successive pulses representing a sequence of Raman movie frames. This capability could be used, for example, to monitor a chemical reaction in progress with a single-shot measurement or to conduct high throughput Raman microscopy.

Example 2

In order to demonstrate the utility of Raman-post amplification for the present invention and other spectroscopic signals, apparatus was used to amplify weak spectroscopic signals. The detection of weak signals presents a significant challenge in many spectroscopic measurements. This issue is especially important in single-shot applications since it is not possible to use averaging to reduce noise. For example, the use of dispersion to chirp the signal typically weakens the signal because dispersive elements usually have significant loss. Optical amplification of the signal may be necessary to resolve this problem.

Unfortunately, traditional optical amplifiers are generally only available for a limited number of restricted wavelength bands. On the other hand, Raman amplifiers are not fundamentally tethered to specific wavelengths, but can operate wherever suitable continuous-wave Raman pumps and gain media are available. Distributed Raman amplification is particularly useful because it can be implemented directly in the dispersive medium to reduce loss or even yield net gain. In DCF, for example, fairly broadband signals can be uniformly amplified and simultaneously dispersed using multiple Raman pump lasers spaced over suitable wavelength intervals.

In spectroscopy, however, coherent pumping may not be necessary to obtain useful Raman post-amplification in many situations. If the noise floor of the detector or digitizer is the limiting factor for the measurement, it is possible to improve the detection threshold using incoherently-pumped Raman amplification. The advantage of this approach is that a single broadband source of intense amplified spontaneous emission (ASE) can be used to produce uniform Raman gain instead of multiple coherent pump lasers. One deficiency of this approach is that the noise of the incoherent light is transferred to the signal. However, ASE-pumped distributed Raman amplification can be utilized to provide broadband optical amplification with acceptable noise transfer.

Figure 10:
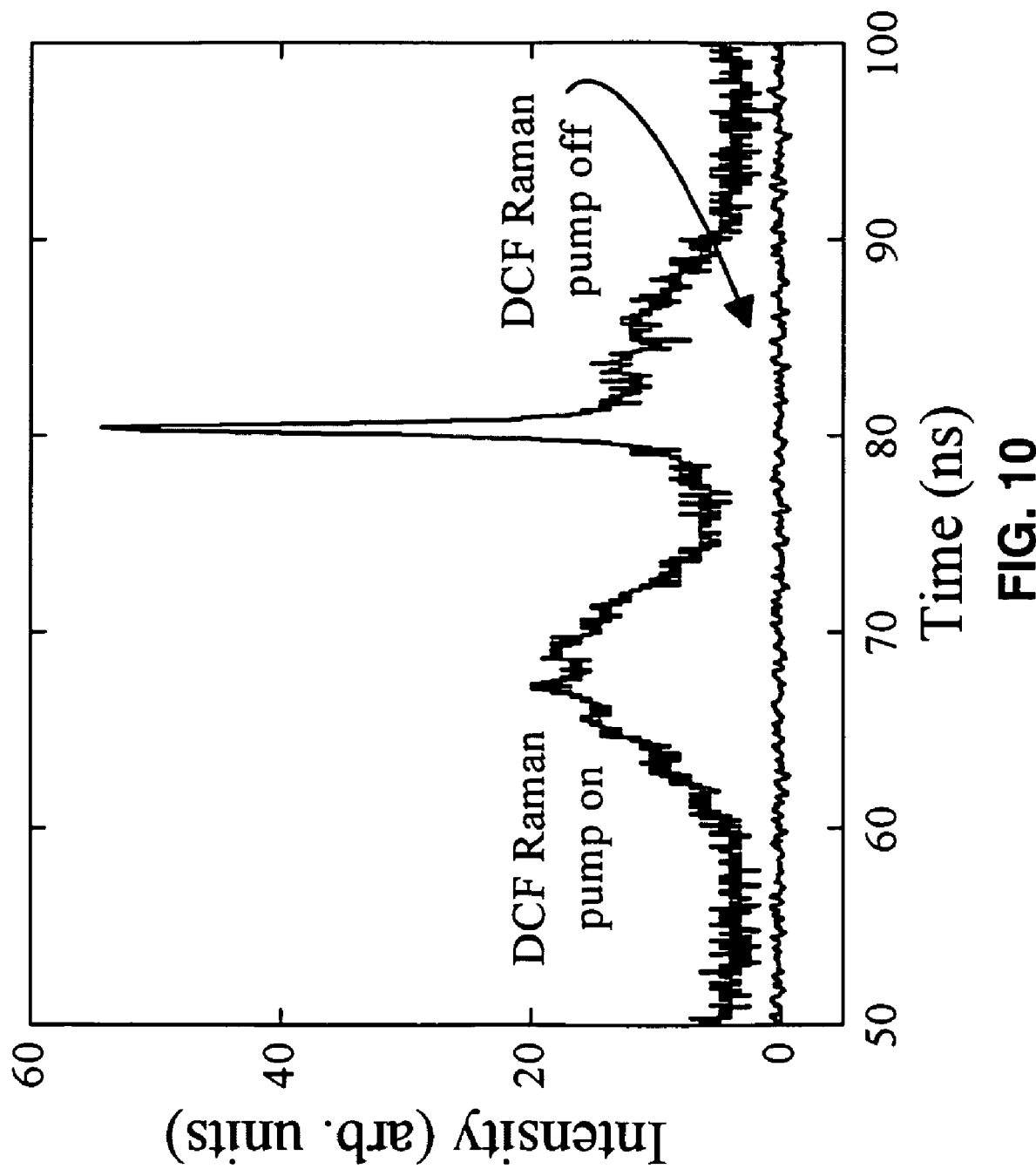
FIG. 10 are experimental results of ASE-pumped Raman post-amplification applied to detect a weak signal using the apparatus of FIG. 2.

Turning now to FIG. 10, the results of an experimental demonstration of the utility of ASE-pumped Raman post-amplification of spectroscopic signals are shown by Raman amplifying a weak SRS signal (produced by stimulated Raman gain using a 50 picosecond pulsed pump at 1550 nm and a supercontinuum probe at 1685 nm with 10 nm width, as described above in FIG. 2) directly in the dispersive DCF medium using a broadband ASE pump.

The ASE pump is produced by a CL-band EDFA with no coherent input and the spectral content of the ASE pump was such that the entire signal could be uniformly amplified given the Raman response of the dispersive (DCF) medium. The ASE pump was coupled into the DCF medium along with the signal using a wavelength-division multiplexer (WDM). Accordingly, the signal was amplified by the Raman gain of the DCF medium and simultaneously dispersed. At the output of the dispersive medium, the pump was separated from the signal using another WDM and the signal was sent to a photodetector whose electrical output is monitored by a 20 gigasample/second real-time oscilloscope. Although noise transferred to the signal during the process, the amplification allows an otherwise undetectable signal to be measured.

It can be seen from the results shown in FIG. 10, that without Raman post-amplification, the signal is undetectable. However, with the post-amplification performed directly in the dispersive medium, the signal is well above the detection threshold.

It can be seen that the invention may have many different high throughput screening and detecting applications. Combinatorial chemistry involves the rapid synthesis of a large number of compounds, which are typically screened for medicinal or materials science applications. Using the high throughput capabilities of the invention, a large number of compounds can be spectrally identified and screened in a short period of time. For example, often a micro-well plate is used to contain the numerous compounds during the synthesis process in combinatorial chemistry. This plate can be used for high throughput screening with the apparatus by either scanning the pump and probe beams across the wells (e.g. with an acousto-optic modulator) or vice versa (e.g., with a piezo-actuated translation stage or high-speed stepper motor). The concept of matched detection can also be applied to spectroscopic screening of combinatorial synthesis. By cross-correlating the measured spectra with known spectral libraries of compound and chemical functional groups, molecules can be detected with high sensitivity. Furthermore, the concept of stimulated matched detection (SMD) described above can also be applied to search for a particular set of compounds or functional groups in the optical domain.

The apparatus and methods can also be applied to the spectroscopy of biomolecules and pathogens. The high throughput capabilities would allow the screening a large number of molecules, microbial species, and disease-causing agents in a short time. Furthermore, since the invention is a single-shot method and nonlinear Raman interactions allow sub-wavelength resolution (especially with tip-enhanced Raman techniques), the metabolism of a single cell or activity of a single viral particle, as well as the structure of single protein molecules and other biological macromolecules can be directly monitored and studied in the time domain. The techniques of matched detection can also be applied to these studies.

Similarly, the apparatus and methods can be used in cancer cell screening. It is known that cancerous cells and tissues can often be identified by their spectroscopic signatures. In certain types of cancer screening studies, a large number of cells must be screened to determine if one out of millions is cancerous. Unfortunately, existing techniques for screening the cells are slow and have some margin of error. These methods also typically require a somewhat lengthy sample preparation involving staining cells with a fluorescent dye. Then, the cells are imaged by laser-excited fluorescence through a microscope. Scanning the cells is a lengthy process because the amount of fluorescence is relatively weak, and imaging requires long integration times. Using stimulated Raman spectroscopy or CARS, cancer cells can be identified without the need for preparation with fluorescent dyes. Since these spectroscopic methods are stimulated rather than spontaneous, the scattered signals can be much more intense. SRS and CARS can also be used for microscopy as previously described, which makes them ideal for cell screening.

The technique of chirped wavelength encoding and electronic time-domain sampling can also be applied to a variety of other spectroscopic techniques. For example, time-domain detection can be utilized in two-photon absorption spectroscopy. Similar to the method described above, if an intense pump beam and a weaker continuum probe pulse are simultaneously introduced into a sample, the sample's two-photon absorption spectrum will be encoded onto the continuum probe. Dispersion can be used to map the spectrum of this encoded pulse into a time-domain waveform by chirping the probe either before or after interaction with the sample. The spectrum can then be detected, electronically sampled, and stored or processed.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method of performing stimulated Raman spectroscopy of a sample, comprising:
    exposing a sample to beams of pulsed probe light;
    exposing said sample to at least one beam of a second light during said exposure of said probe light;
    mapping a spectrum of light scattered from said sample into a time-domain waveform with a plurality of dispersive elements so that the spectra is detected directly in the time domain to provide a mapped time-domain waveform; and
    detecting said mapped time-domain waveform.

2. A method as recited in claim 1, further comprising:
    dispersing said spectrum of light scattered from said sample prior to detection.

3. A method as recited in claim 1, further comprising:
    exposing said sample to beams of dispersed light and said second light simultaneously.

4. A method as recited in claim 1, wherein said probe beams are derived from a supercontinuum of light.

5. A method as recited in claim 1, further comprising:
    converting light scattered from said sample to electronic signals.

6. A method as recited in claim 5, further comprising:
    filtering said electronic signals;
    amplifying said filtered electronic signals;
    converting said amplified and filtered electronic signals to digital signals; and
    processing said digital signals.

7. A method as recited in claim 1, further comprising:
    directing light scattered from said sample through a dispersive element; and
    amplifying light within said dispersive element.

8. A method as recited in claim 1, further comprising:
    mixing a local oscillator beam with light beams scattered from said sample; and
    detecting said mixed beams with an optical detector.

9. A method as recited in claim 8, wherein said local oscillator beam comprises a continuous wave beam or an independent pulse.

10. A method as recited in claim 1, further comprising:
    splitting beams of dispersed, pulsed light to provide an incident pulse and a local oscillator pulse;
    amplifying said local oscillator pulse;
    inserting a time delay in said local oscillator pulse;
    combining said local oscillator pulse with light scattered from said sample; and
    detecting said combined beams with an optical detector.

11. A method as recited in claim 10, further comprising:
    converting said combined beams to an electronic signal;
    converting said electronic signal into a digital signal;
    processing said digital signals; and
    analyzing said digital signals for phase information.

12. A method as recited in claim 1, further comprising:
    performing time-division multiplexing of said pulsed light.

13. A method as recited in claim 1, further comprising:
    matching spectra obtained from said sample with a library of spectra to identify a chemical species present in the sample.

14. A method as recited in claim 1, further comprising:
    preparing dispersed pulsed probe light with a spectrum matching the spectrum of a selected chemical species; and
    exposing said sample with said modulated light for stimulated matched detection.

15. A method as recited in claim 1, further comprising:
    enhancing Raman scattering signals with colloidal metal nanoparticles in suspension in a Raman medium.

16. A method for conducting Raman microscopy of a sample, comprising:
    placing a sample in proximity to a metal probe;
    exposing said sample to beams of chirped, pulsed laser light;
    exposing said sample to at least one beam of light during said exposure of chirped, pulsed laser light;
    mapping a spectrum of light scattered from said sample into a time domain waveform to produce a mapped time domain waveform; and
    characterizing said mapped time domain waveform.

17. A method as recited in claim 16, further comprising:
    amplifying said pulsed laser light to generate a supercontinuum of light; and
    filtering said light from said continuum prior to dispersion.

18. A method as recited in claim 16, further comprising:
    converting light scattered from said sample to electronic signals.

19. A method as recited in claim 18, further comprising:
filtering said electronic signals;
amplifying said filtered electronic signals;
converting said amplified and filtered electronic signals to digital signals; and
processing said digital signals.

20. A method as recited in claim 16, further comprising:
placing said sample on a surface in proximity to a metal tip.

21. A method of spontaneous Raman spectroscopy, comprising:
exposing a sample to a beam of pulsed light;
dispersing temporally light emitted from said sample;
mapping a spectrum of light scattered from said sample into a time domain waveform; and
characterizing said time domain waveform.

22. A method as recited in claim 21, further comprising:
optically amplifying said temporally dispersed light; and
detecting said amplified light with an optical detector.

23. A method as recited in claim 21, further comprising:
converting temporally dispersed light scattered from said sample to electronic signals.

24. A method as recited in claim 23, further comprising:
filtering said electronic signals;
amplifying said filtered electronic signals;
converting said amplified and filtered electronic signals to digital signals; and
processing said digital signals.

25. An apparatus for performing Raman spectroscopy of a sample, comprising:
a pulsed probe laser;
a dispersive element operably coupled to said pulsed laser configured to direct temporally dispersed pulsed laser light on a sample;
a Raman pump laser configured to direct laser light on said sample; and
an optical detector;
wherein characteristics of light scattered from said sample during exposure to said laser light are mapped directly in a time domain.

26. An apparatus as recited in claim 25, wherein said dispersive element is selected from the group of dispersive elements consisting essentially of an optical fiber, an optical grating, a chirped mirror, and a prism.

27. An apparatus as recited in claim 25:
wherein said optical detector comprises at least one detector selected from the group of detectors consisting essentially of an avalanche photodiode, a p-i-n photodiode and a photomultiplier tube,
wherein light scattered from said sample is converted to electronic signals by said detector.

28. An apparatus as recited in claim 27, further comprising:
an electrical filter electrically coupled to said detector;
an electrical amplifier coupled to said electrical filter;
an analog to digital signal converter; and
means for digital signal processing,
wherein electrical signals from said detector are sequentially filtered, amplified, digitized and processed.

29. An apparatus as recited in claim 28, further comprising:
means for electronically cross correlating a digital signal with a library of signals of known Raman spectra.

30. An apparatus as recited in claim 25, said pulsed probe laser further comprising:
an optical amplifier configured to optically amplify light from said probe laser;
a supercontinuum element coupled to said amplifier; and
an optical filter configured to filter light from said supercontinuum element.

31. An apparatus as recited in claim 25, further comprising:
a second dispersive element configured to receive and disperse light scattered from said sample; and
an optical amplifier,
wherein light scattered from said sample is dispersed and amplified before optical detection.

32. An apparatus as recited in claim 25, further comprising:
means for performing stimulated matched detection of chemical species in said sample.

33. An apparatus as recited in claim 32, wherein said means for performing stimulated matched detection of chemical species comprises an electro-optic modulator.

34. An apparatus as recited in claim 32, wherein said means for performing stimulated matched detection of chemical species comprises time-domain modulation of said dispersed pulsed probe laser beam.

35. An apparatus as recited in claim 25, wherein said optical detector comprises:
a coherent optical detector adapted to generate a signal from which the phase of a time-domain waveform is recovered.

36. An apparatus as recited in claim 35, wherein said coherent optical detector comprises an optical mixer.

37. An apparatus as recited in claim 35, wherein said coherent optical detector further comprises frequency-resolved optical gating.

38. An apparatus as recited in claim 35, wherein said coherent optical detector further comprises an interferometer.

39. An apparatus as recited in claim 25, further comprising:
an optical multiplexer optically coupled to said probe laser.

40. An apparatus for Raman spectroscopy, comprising:
a pulsed probe laser;
a first dispersive element operably coupled to said pulsed probe laser configured to direct temporally dispersed pulsed laser light on a sample;
a Raman pump laser configured to direct laser light on said sample;
a second dispersive element adapted to receive and disperse light scattered from said sample during exposure to said pulsed laser light and said Raman pump laser light; and
means for analyzing characteristics of light scattered from said sample sampled within a time domain.

41. An apparatus as recited in claim 40, wherein said means for analyzing characteristics of light scattered from said sample comprises:
an optical amplifier configured to amplify light scattered from said sample;
an optical detector configured for converting light from said optical amplifier to electronic signals;
an analog to digital signal converter; and
a digital signal processor,
wherein electronic signals from said optical detector are digitized and processed.

42. An apparatus as recited in claim 40, wherein said first and second dispersive element are selected from the group of dispersive elements consisting essentially of an optical fiber, an optical grating, a chirper mirror and a prism.

43. An apparatus as recited in claim 40, wherein said second dispersive element has a sign opposite to a sign of said first dispersive element.

44. An apparatus for Raman Microscopy, comprising:
a source of a plurality of chirped, pulsed probe beams directed to a sample;
a source of a plurality of Raman pump beams directed to a sample; and means for detecting characteristics of light scattered from exposure of a sample to at least one of said probe beams and at least one of said pump beams within a time domain.

45. An apparatus as recited in claim 44, further comprising:

a pointed metal tip disposed in close proximity to a focal point of said probe beams and said pump beams on said sample.

46. An apparatus as recited in claim 45, wherein said pointed metal tip is a metal selected from the group of metals essentially comprising: silver, gold and copper.

47. An apparatus as recited in claim 44, further comprising:

means for sweeping a focal point of said probe beam and said pump beam across a sample;

wherein a high resolution Raman image of the sample is obtained.

48. An apparatus as recited in claim 45, further comprising:

means for sweeping a focal point of said probe beam and said pump beam and said metal tip across a sample;

wherein an enhanced high resolution Raman image of the sample is obtained.

49. An apparatus as recited in claim 44, further comprising:

means for scanning a sample in three dimensions and displaying a composite image of the sample.

50. An apparatus as recited in claim 44, wherein said means for detecting characteristics of scattered light comprises:

an optical detector configured for converting light into electronic signals; and a display.

51. An apparatus as recited in claim 44, wherein said means for detecting characteristics of scattered light comprises:

an optical detector configured for converting light into electronic signals;

an analog to digital signal converter;

a computation device for digital signal processing and formulation of Raman spectra; and a display.

52. An apparatus as recited in claim 51, further comprising:

an electrical signal filter; and an amplifier, wherein electronic signals from said optical detector are filtered and amplified prior to digital conversion by said analog to digital converter.

53. An apparatus as recited in claim 44, wherein said means for detecting characteristics of scattered light comprises:

a dispersive element optically coupled to a light source;

an optical amplifier amplifying dispersed light from said dispersive element;

an optical detector configured for converting amplified light into electronic signals;

an analog to digital signal converter coupled to said detector;

a computation device for digital signal processing and formulation of Raman spectra from a digitized signal; and a display.

54. An apparatus as recited in claim 51, further comprising:

an electrical signal filter; and an amplifier, wherein electronic signals from said optical detector are filtered and amplified prior to digital conversion by said analog to digital converter.

\* \* \* \* \*